(12) United States Patent
Soss et al.

(10) Patent No.: US 9,089,444 B2
(45) Date of Patent: Jul. 28, 2015

(54) VALVE FOR PROSTHESIS ATTACHMENT

(71) Applicants: Adam Soss, Winnetka, CA (US); Dustin Bouch, Petaluma, CA (US)

(72) Inventors: Adam Soss, Winnetka, CA (US); Dustin Bouch, Petaluma, CA (US)

( * ) Notice: Subject to any disclaimer, the term of this patent is extended or adjusted under 35 U.S.C. 154(b) by 56 days.

(21) Appl. No.: 13/945,715

(22) Filed: Jul. 18, 2013

(65) Prior Publication Data
US 2014/0067084 A1  Mar. 6, 2014

Related U.S. Application Data

(60) Provisional application No. 61/695,171, filed on Aug. 30, 2012.

(51) Int. Cl.
*A61F 2/80* (2006.01)
*A61F 2/78* (2006.01)

(52) U.S. Cl.
CPC ... *A61F 2/80* (2013.01); *A61F 2/78* (2013.01); *A61F 2002/805* (2013.01)

(58) Field of Classification Search
CPC .............................. A61F 2/80; A61F 2002/805
USPC ..................................... 623/34; 251/280, 289
See application file for complete search history.

(56) References Cited

U.S. PATENT DOCUMENTS

| | | | |
|---|---|---|---|
| 4,564,365 A | 1/1986 | Winer et al. | |
| 5,139,523 A | 8/1992 | Paton et al. | |
| 5,490,537 A | 2/1996 | Hill | |
| 5,658,353 A | 8/1997 | Layton | |
| 5,702,489 A | 12/1997 | Slemker | |
| 5,728,170 A | 3/1998 | Becker et al. | |
| 5,895,429 A | 4/1999 | Cool et al. | |
| 6,063,125 A | 5/2000 | Arbogast et al. | |
| 6,079,445 A | 6/2000 | Huang | |
| 6,287,345 B1 | 9/2001 | Slemker et al. | |
| 6,334,876 B1 * | 1/2002 | Perkins | 623/34 |
| 6,440,173 B1 | 8/2002 | Meyer | |
| 7,172,580 B2 | 2/2007 | Hruska et al. | |
| 7,448,407 B2 | 11/2008 | Alley et al. | |
| 7,631,657 B2 | 12/2009 | Alley et al. | |
| 7,827,984 B2 | 11/2010 | Von Schuckmann | |
| 7,993,413 B2 | 8/2011 | Perkins et al. | |
| 8,113,235 B2 * | 2/2012 | Bogue | 137/522 |
| 2011/0130846 A1 | 6/2011 | Kampas et al. | |

FOREIGN PATENT DOCUMENTS

WO  WO-2007001745 A2  1/2007

OTHER PUBLICATIONS

International Search Report and Written Opinion issued in International Application PCT/US2013/051095, mailed Nov. 6, 2013.

* cited by examiner

*Primary Examiner* — Bruce E Snow
(74) *Attorney, Agent, or Firm* — Mintz Levin Cohn Glovsky and Popeo, P.C.

(57) ABSTRACT

Devices, systems, and methods relating to a valve that may be used with a prosthesis attachment include a valve assembly that includes a spring loaded insert portion and a base portion that interfaces to lock and unlock by depressing the spring loaded insert portion.

19 Claims, 16 Drawing Sheets

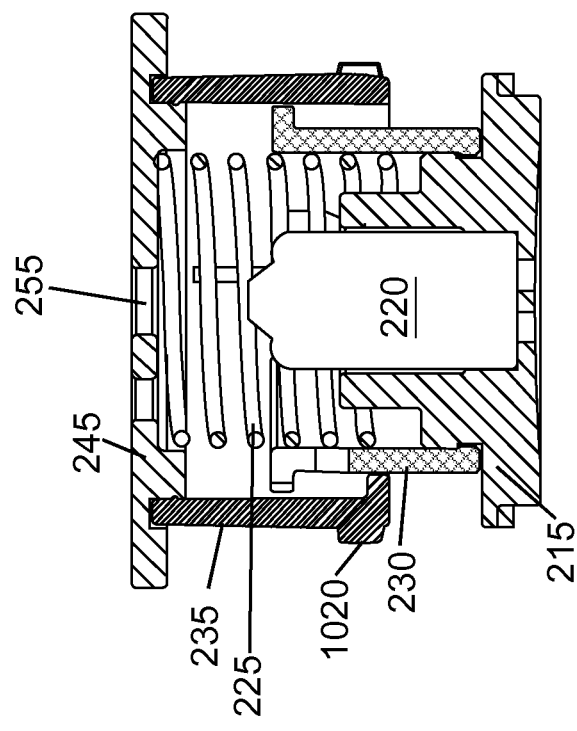
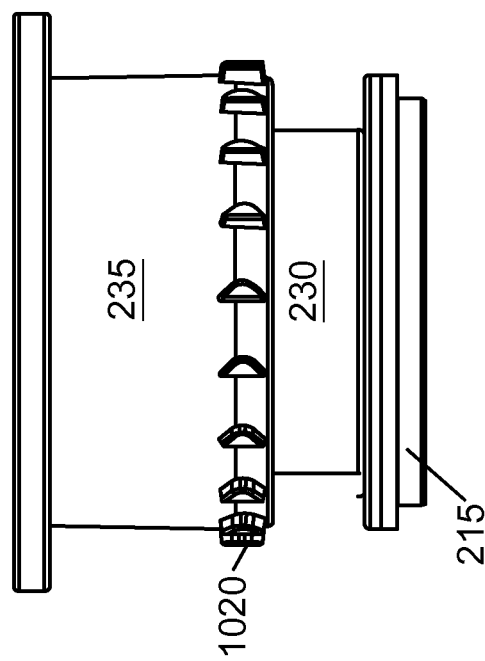
FIG. 4

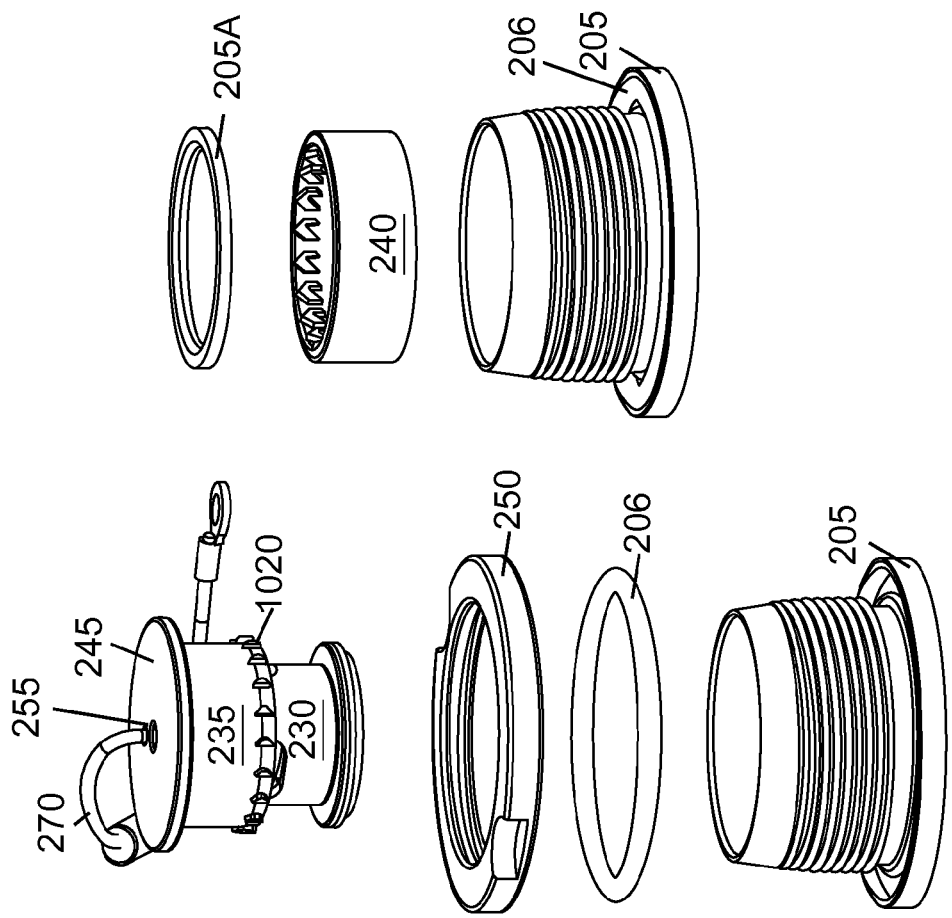
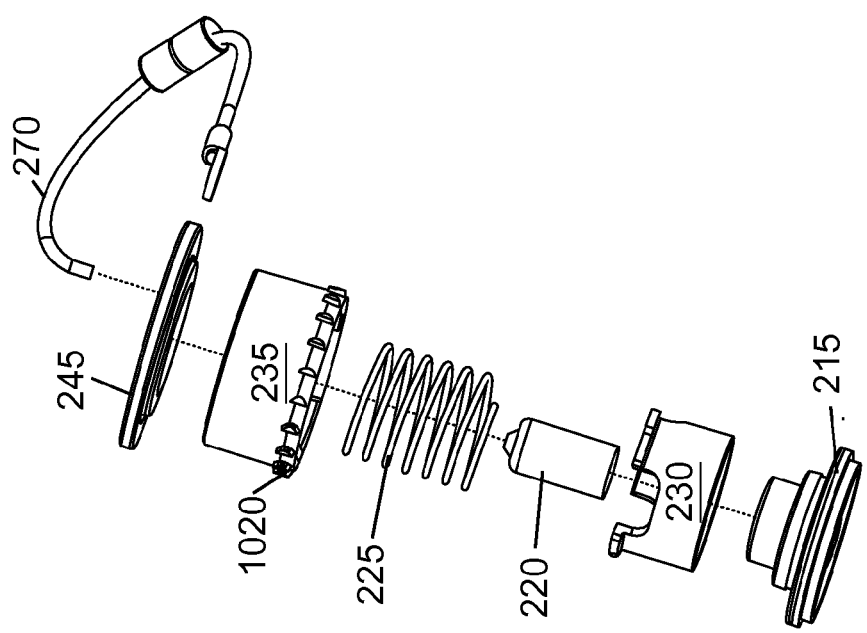

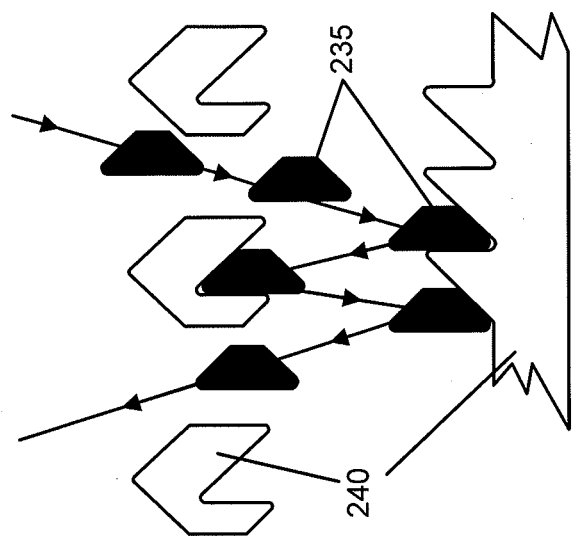
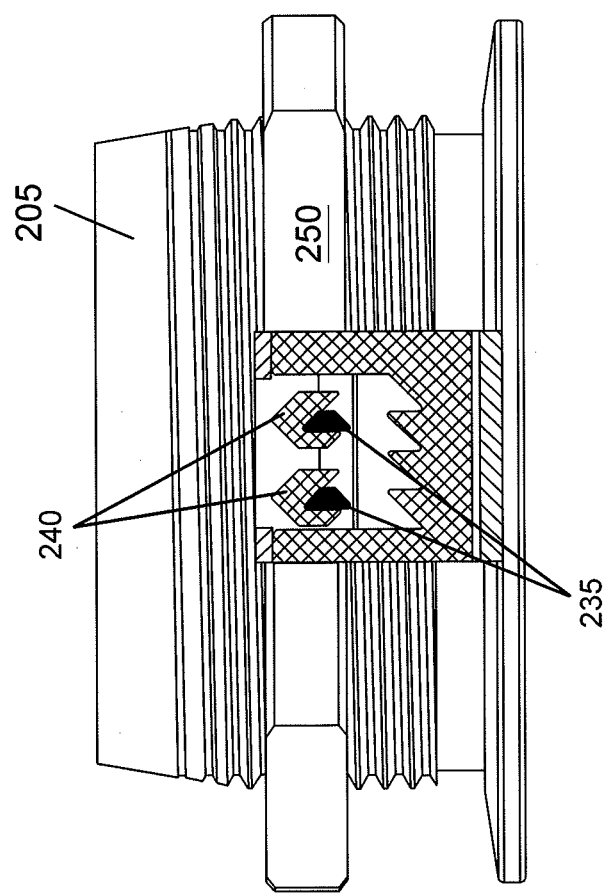
FIG. 6

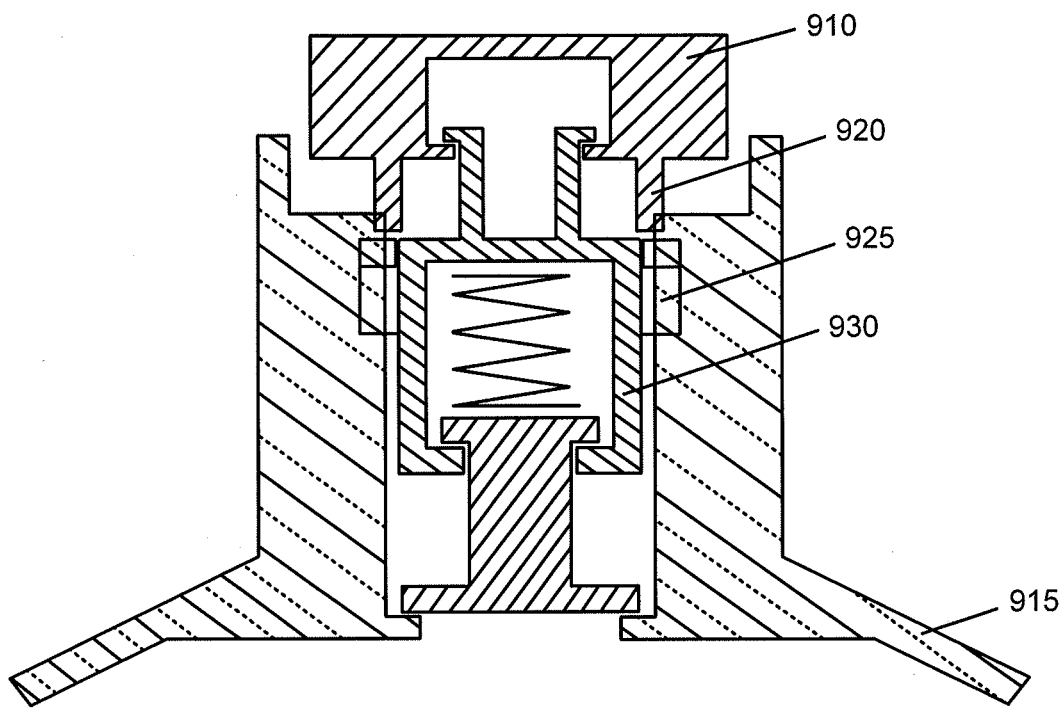
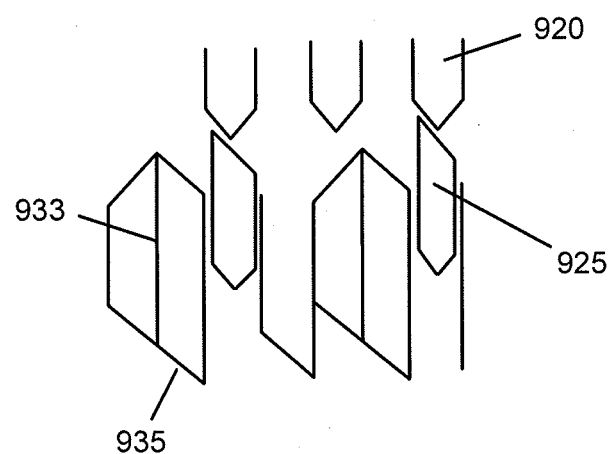
FIG. 9

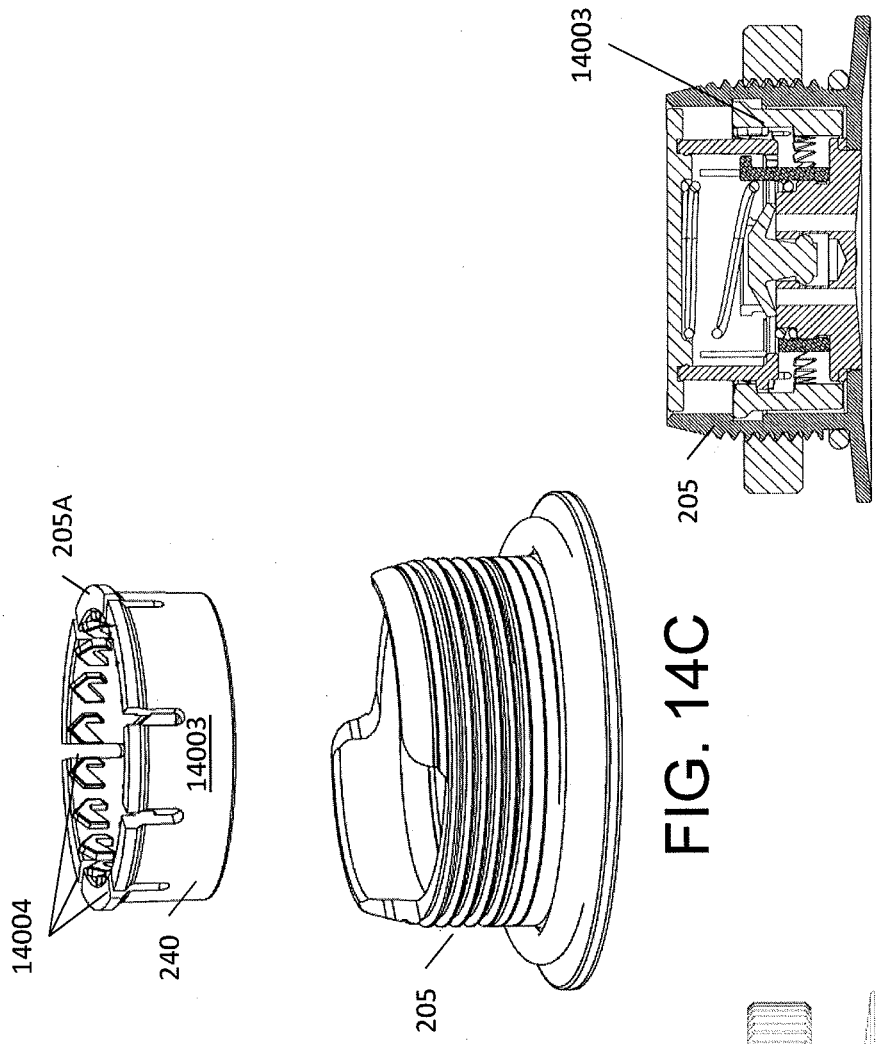

VALVE FOR PROSTHESIS ATTACHMENT

CROSS REFERENCE TO RELATED APPLICATIONS

This application claims priority to U.S. Provisional Patent Application No. 61/695,171, filed Aug. 30, 2012, and titled, "Valve for Prosthesis Attachment," the disclosure of which is hereby incorporated by reference in its entirety.

BACKGROUND

Placement of a prosthesis into an attachment location on the limb of a patient utilizes a valve that maintains a negative pressure to suspended the prosthesis in the attachment location. Valves that are currently used in this capacity are often threaded or include cumbersome latching designs. Such valves can require significant hand dexterity that can be difficult for a patient.

SUMMARY

In some implementations, the current subject matter relates to a valve, a valve assembly, and methods for maintaining negative pressure to suspend a limb. The valve assembly can have a spring loaded inserted portion and base portion that a patient or user can cause to interface and lock. Expulsion of extra air or other gas from the prosthesis attachment point can be achieved by pressing down on the prosthetic limb as the air moves through a one-way valve within the valve assembly.

Presented herein in some implementations, a valve assembly is provided that includes a base that is outside a bottom portion. The bottom portion includes an inner containment ring. The valve assembly also include a one-way valve with an inlet and an outlet configured to fit inside the inner containment ring. A spring, a latching actuating ring, and an indexing ring are also included in the valve assembly. The spring is outside of the one-way valve and fits inside the inner containment ring. The latching actuating ring is configured to fit over the inner containment ring, and the latching actuating ring includes, or attaches to, a top cap. The latching actuating ring includes teeth positioned around a portion of the latching actuating ring. The top cap can include an air passage configured to be in fluid communication with the outlet of the one-way valve. The teeth of the latching ring are positioned on an outer, lower portion of the latching actuating ring. The indexing ring is configured to interact with the teeth on the latching actuating ring.

The following features can be present in the valve assembly in any suitable combination. The base of the valve assembly can also include a threaded outer portion. The base can include a bottom cap that interfaces with the inlet of the one-way valve. The valve assembly can include a lanyard connected to the top cap and configured to attach to a point on a surface into which the valve assembly inserts in some implementations. In such implementations, the surface into which the valve assembly inserts can be a prosthetic limb. The indexing ring can include a snap fit portion located at a top portion of the indexing ring, the snap fit portion configured to maintain the indexing ring inside the base when the valve assembly is in use. The valve assembly can further include a seal on a bottom side of the bottom portion in some implementations. The inner containment ring can include tabs and the latching actuating ring can include receiving cut outs configured to match the tabs.

In a related aspect, provided in some implementations is a prosthesis that includes a valve assembly and a prosthesis attachment site. The valve assembly includes a base, a one-way valve, a spring, a latching actuating, and an indexing ring. The base is outside a bottom portion that includes an inner containment ring. The one-way valve has an inlet and an outlet configured to fit inside the inner containment ring. The spring that is outside the one-way valve also fits inside the inner containment ring. The latching actuating ring of the valve assembly of the prosthesis is configured to fit over the inner containment ring. The latching actuating ring attaches to a top cap that can include an air passage configured to be in fluid communication with the outlet of the one-way valve and teeth position around an outer, lower portion of the latching actuating ring.

The features below can be present in the prosthesis in any suitable combination. The valve assembly of the prosthesis can include a lanyard connected on the top cap and configured to attach to a point on a surface of the prosthesis. The indexing ring can include a snap fit portion located at a top portion of the indexing ring, the snap fit portion can be configured to maintain the indexing ring inside the base when the valve assembly is in use. The valve assembly can also include a seal on a bottom side of the bottom portion in some implementations of the prosthesis. The inner containment ring of the valve assembly of some implementations of the prosthesis can include tabs and the latching actuating ring comprises receiving cut outs configured to match the tabs. In some implementations, the indexing ring interacts with the teeth of the latching actuating ring through indexing teeth located on the indexing ring, and the indexing teeth can be configured to induce a motion of the indexing ring when the latching actuating ring is moved vertically over the indexing ring. The indexing ring can include upper and lower teeth, the upper teeth shaped as elongated hexagons and the lower teeth having receiving recesses.

Further, in another related aspect, provided in some implementations is a method of creating and maintaining negative pressure in an attachment site in a prosthetic limb that includes providing a prosthetic limb that includes a valve assembly. The prosthetic limb includes a valve assembly that includes a base, a one-way valve, a spring, a latching actuating ring, and an indexing ring. The base is outside a bottom portion that includes an inner containment ring, and the one-way valve is configured to fit inside the inner containment ring. The one-way valve also has an inlet and an outlet. The spring is outside of the one-way valve and fits inside the inner containment ring. The latching actuating ring is configured to fit over the inner containment ring. The latching actuating ring includes a top cap that can include an air passage that is configured to be in fluid communication with the outlet of the one-way valve and an indexing ring that is configured to interact with the teeth on the latching actuating ring.

The following features can be present in the method of creating and maintaining negative pressure in an attachment site in a prosthetic limb in any suitable combination. The method can further include moving a patient's limb towards the prosthesis attachment side of the prosthetic limb to expel air from a space between the prosthesis and a patient's limb within the prosthesis attachment site. The indexing ring can interact with the teeth of the latching actuating ring through indexing teeth located on the indexing ring, the indexing teeth can be configured to induce a motion of the indexing ring when the latching actuating ring is moved vertically over the indexing ring in some implementations. In such implementations, the upper driving teeth can be angled on each side, such that the upper driving teeth resemble a component of a picket fence configuration and the lower driving teeth on the indexing ring driver are angled towards only one direction.

The indexing ring can include a snap fit portion location at a top portion of the indexing ring, the snap fit portion configured to maintain the indexing ring inside the base when the valve assembly is in use.

In another related aspect, in some implementations a suction socket prosthetic valve assembly that includes a top and a bottom, in which the valve assembly is configured to alternatively lock into a first position and unlock when force is applied to the top to direct the top towards the bottom is provided. The suction socket prosthetic valve assembly is configured such that a first applied force causes locking into the first position, and a second applied force causes unlocking.

The following features can be present in the suction socket prosthetic valve assembly in any suitable combination. The suction socket prosthetic valve assembly can include a base that is outside a bottom portion. The bottom portion can include an inner containment ring. The suction socket prosthetic valve assembly can also include a one-way valve with an inlet and an outlet configured to fit inside the inner containment ring. A spring, a latching actuating ring, and an indexing ring can also be included in the suction socket prosthetic valve assembly. The spring can be outside of the one-way valve and can fit inside the inner containment ring. The latching actuating ring can be configured to fit over the inner containment ring, and the latching actuating ring can include, a top cap and teeth positioned around a portion of the latching actuating ring. The top cap can have an air passage configured to be in fluid communication with the outlet of the one-way valve. The portion of the latching actuating ring on which the teeth are positioned can be an outer, lower portion of the latching actuating ring. The indexing ring can be configured to interact with the teeth on the latching actuating ring. In some implementations, the latching actuating ring and the indexing ring can interact to alternately lock and unlock the suction socket prosthetic valve assembly when force is applied. The indexing ring can interact with the teeth of the latching actuating ring through indexing teeth located on the indexing ring, and the indexing teeth can be configured to induce a motion of the indexing ring when the latching actuating ring is moved vertically over the indexing ring. The indexing ring can include a snap fit portion located at a top portion of the indexing ring, and the snap fit portion can be configured to maintain the indexing ring inside the base when the valve assembly is in use.

BRIEF DESCRIPTION OF THE DRAWINGS

The current subject matter is described with reference to the accompanying drawings. In the drawings, like reference numbers indicate identical or functionally similar elements.

FIG. 4 illustrates an insert portion of a valve assembly including a latching actuating ring and an inner containment ring in an inserted and locked configuration.

FIGS. 5A, 5B, and 5C show an exploded view of a valve assembly.

FIG. 6 illustrates an implementation of teeth on the insert portion interacting with a rotating latch ring on the base of a valve assembly.

FIG. 9 shows an alternate locking mechanism design for a valve assembly.

FIGS. 14A, 14B, 14C, and 14D show another implementation of a valve assembly.

DETAILED DESCRIPTION

As stated above, some embodiments of the current subject matter relate to valves and valve assemblies used in the attachment of prosthetic limbs to patients. The valves currently in use often require a level of hand dexterity that is beyond that of many patients. The valve designs described herein, which do not require threads or latches, are simple to use and readily maintain a locked position.

Figure 1A:
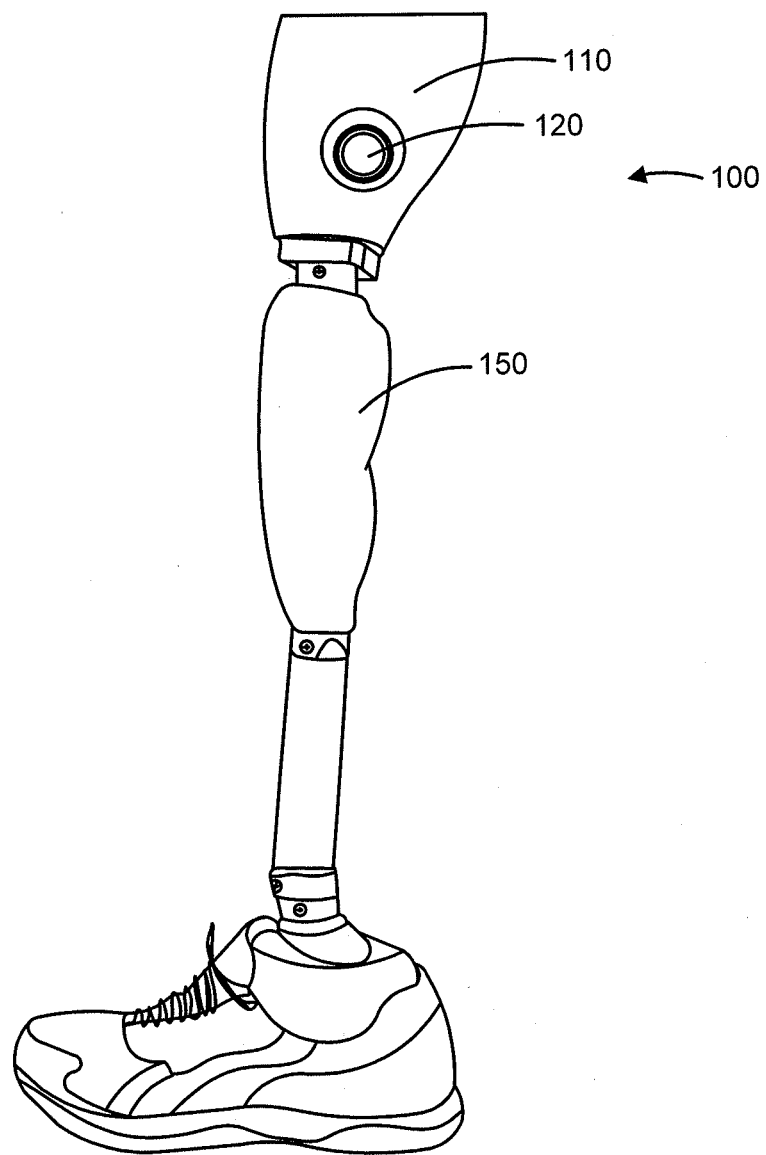
FIGS. 1A and 1B illustrate an exemplary prosthesis and attachment site assembly, including a valve.
Figure 1B:
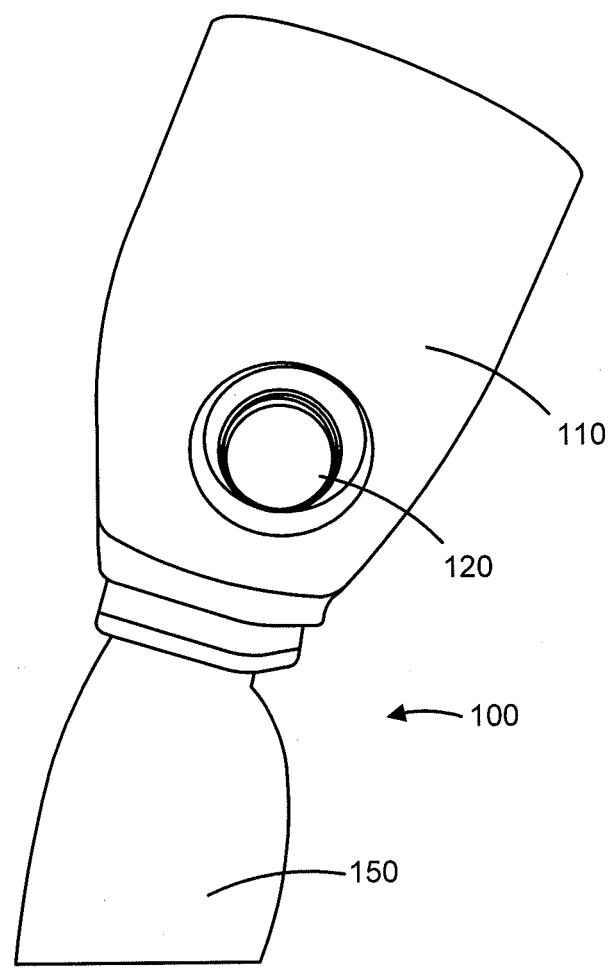

FIGS. 1A and 1B show a prosthesis and attachment site assembly 100 for a leg. The prosthesis attachment site, or socket portion of the prosthesis, 110 includes a valve 120 that maintains a negative pressure on the prosthesis and keeps the prosthesis suspended. The valve 120, is shown in its assembled state, with a spring loaded valve portion inserted into the valve base. Below the prosthesis attachment site, or socket, 110 is the rest of prosthesis 150.

Figure 2:
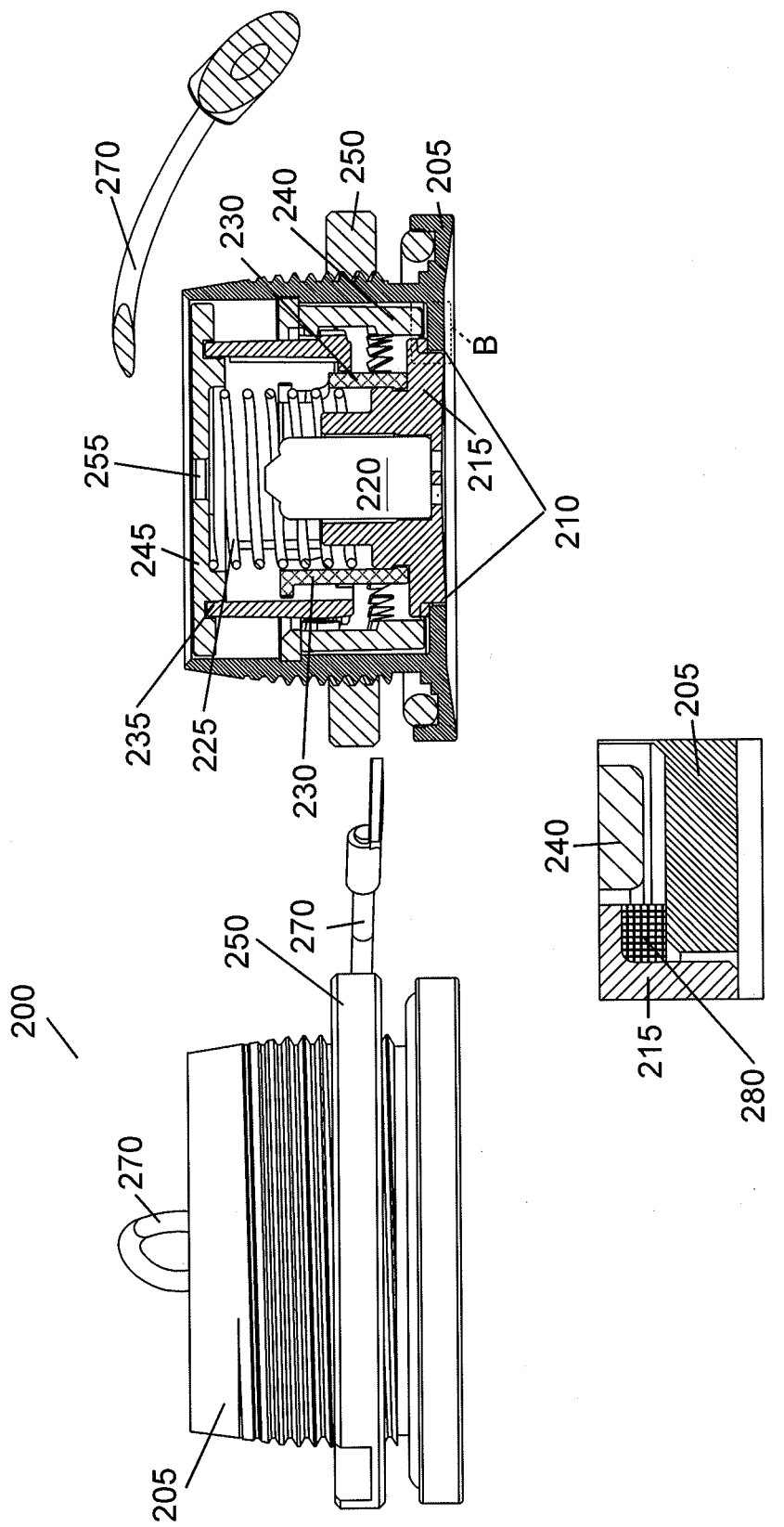
FIG. 2 illustrates a valve assembly in an inserted and locked configuration.

FIG. 2 illustrates a valve assembly 200 in an inserted and locked configuration. The valve assembly 200 has a base 205 with a threaded outer portion and an inner portion that is outside a spring loaded insert 210. The base 205 can surround, completely or at least partially, the spring loaded insert 210. The spring loaded insert 210 includes a bottom cap 215, a one-way valve 220, a spring 225, an inner containment ring 230, a latching actuating ring 235, and a top cap 245. The spring loaded insert 210 is surrounded by a rotating latch ring 240, inside the base 205. The rotating latch ring 240 is outside the spring loaded insert 210, at least partially, and the rotating latch ring 240 may or may not be removable from base 205. At the center of the top cap 245 there may be an orifice that defines an air passage 255 for gas expelled through the one-way valve 220 to pass.

The one-way valve can be in fluid communication with the volume beneath the valve assembly when it is seated in an attachment site of a prosthetic limb. When the one-way valve is in fluid communication with the volume in the attachment site beneath the valve assembly, the valve assembly allows for air to pass from the prosthetic attachment site, through the valve, to the ambient environment. Removal of air from the prosthetic attachment site can cause negative pressure in the attachment site, which can help the prosthetic adhere to the person wearing the prosthetic.

Around the outside of the base 205 and engaged with the treads, is a threaded ring, or base nut, 250. A lanyard 270 can be attached to the valve assembly 200 at the top cap in FIG. 2. The inset B in FIG. 2 shows a sealing surface 280 in under an undercut in and attached to the bottom cap 215. The sealing surface 280 also interfaces with the base 205 and is potentially in contact with the rotating latch ring 240.

Figure 3:
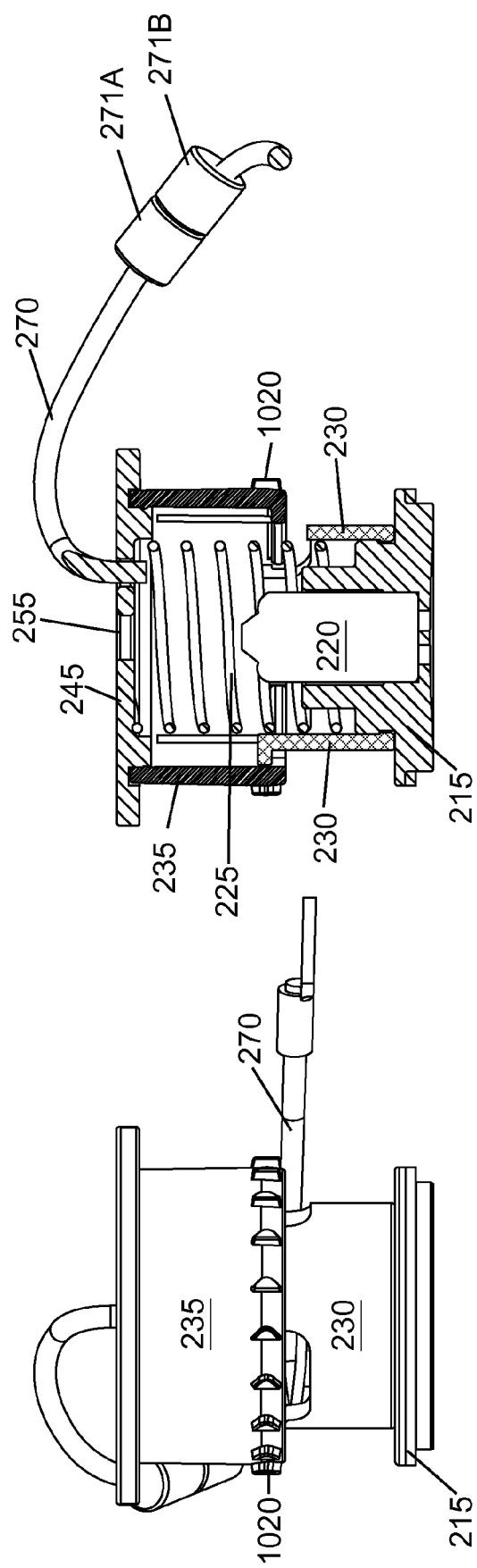
FIG. 3 illustrates an insert portion of a valve assembly including a latching actuating ring and an inner containment ring in an extended configuration.

FIG. 3 shows the spring loaded insert 210 of a valve assembly 200 including a latching actuating ring 235 and an inner containment ring 230 in an extended configuration. Contrastingly, FIG. 4 shows the spring loaded insert 210 of a valve assembly 200 including a latching actuating ring 235 and an inner containment ring 230 in a partially compressed configuration.

FIGS. 5A, 5B, and 5C show an exploded view of a valve assembly 200. The valve assembly 200 is shown in three portions in FIG. 5. Shown in the leftmost portion, FIG. 5A, the spring loaded insert includes the bottom cap 215 that is beneath the inner containment ring 230. In the center of the bottom cap 215 fits the one-way valve 220 and the spring 225, which is sized to fit around the one-way valve 220 and inside the inner containment ring 230. The latching actuating ring 235 fits above the bottom cap 215 and around the inner containment ring 230. The top cap 245 fits above the latching actuating ring 235. The lanyard 270 is attached to the top of the top cap 245.

In FIG. 5B, the bottom portion of the valve 200 is shown in a partially exploded view below the spring loaded insert 210. The base 205 with a threaded outer portion is outside the rotating latch ring 240 that is beneath a retaining ring 205A that also fits within the base 205. The base 205 is outside the rotating latch ring 240, such that it at least partially surrounds the rotating latch ring 240. An o-ring 206 fits into a groove on the base 205 and serves to seal the base to the prosthetic when in use. A threaded ring 250 fits around the base 205 by screwing onto the threads on the base 205. The latching actuating ring 235 with the top cap 245 is also shown. The air passage 255 through the center of the top cap 245 is shown adjacent to the point where the lanyard 270 attaches to the top cap 245. FIG. 5C shows a partially assembled view of the base 205, with the o-ring 206 in place. The rotating latch ring 240, which is also seen in FIG. 2, is shown. In FIG. 5C, the rotating latch ring 240 is removed from the base 205 so that the inner portion of the latch ring can be seen, particularly the portion that interfaces with the latching actuating ring 235. When the rotating latch ring 240 is seated within the base 205, a retaining ring 205A sits above the latch ring 240 to keep it from moving except for in a rotational manner.

FIG. 6 illustrates an implementation of teeth on the latching actuating ring 235 interacting with a rotating latch ring 240 on a valve assembly. The right hand side of FIG. 6 illustrates the latching motion used in the valve assembly shown in FIGS. 2 through 5. When the spring loaded insert 210 (as seen in FIG. 4) is depressed in, teeth located on the latching actuating ring 235, shown in black, slide down over the tops of protrusions in the rotating latch ring 240 and then fit under the protrusions into a locked position. When unlocking is desired, the spring loaded insert 210 is depressed again, the teeth (shown in black) move out from under the protrusions and move free of the latching actuating ring protrusions.

Figure 7:
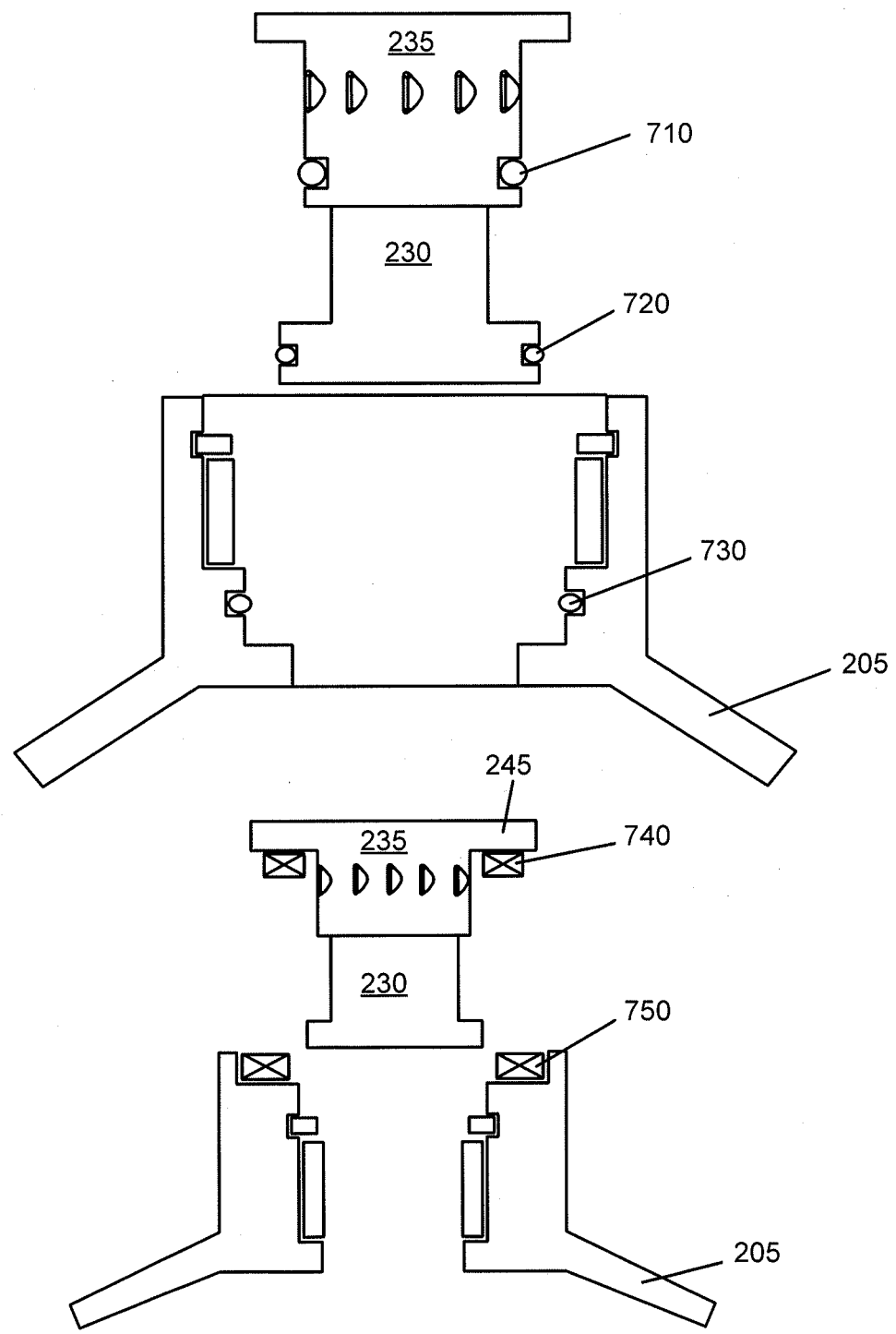
FIG. 7 shows various placement configurations for seals within the valve assembly.

FIG. 7 shows various placement configurations for seals within the valve assembly. The top portion of FIG. 7 shows various possible placements of radial o-ring seals. The first possible location 710 is the outside of the base of the latching actuating ring 235. The second possible location is at 720, at the base of the inner containment ring 230 or bottom cap 215, around the circumference of the inner containment ring 230 or bottom cap 215. A third possible seal location 730 is on the inside of the base 205. The bottom half of FIG. 7 shows two possible locations for rubber or foam lip or face seals. The first possible location for a rubber or foam lip or face seal 740 is on the underside of the cap 245 at the top of the latching actuating ring 235. The second possible location 750 is at the top of the base 205.

Figure 8:
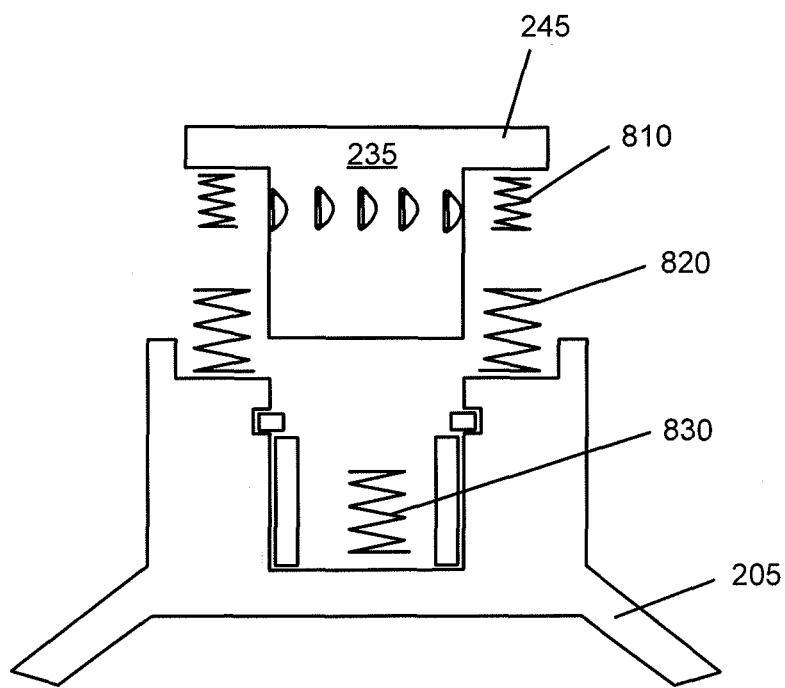
FIG. 8 shows various placement configurations for springs within the valve assembly.

FIG. 8 shows various placement configurations for springs within the valve assembly. Shown are three possible locations for one or more springs in a valve assembly. Springs 810 can be located in an annular pattern underneath the top cap 245, outside the latching actuating ring 235. Alternatively, springs 820 can be located in an annular pattern on a top portion of the base 205. A spring 830 (corresponding to the spring 225 in FIGS. 2-5C) can be located in the interior of the base 205.

Figure 10:
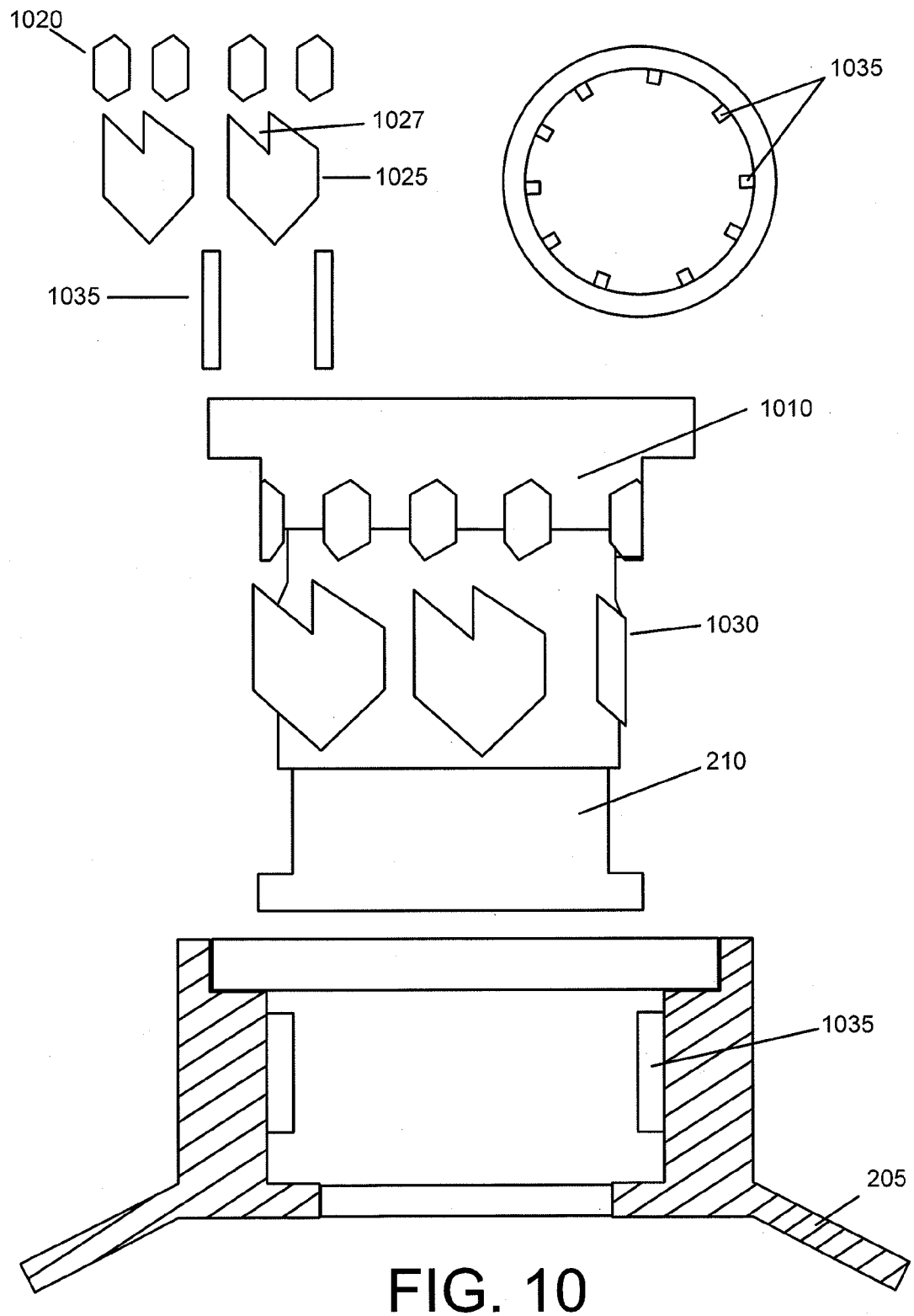
FIG. 10 shows a second alternate locking mechanism design for a valve assembly.

FIGS. 9 and 10 show alternate locking mechanism designs for a valve assembly. The design of FIG. 9 shows a valve assembly that includes a rotating index ring driver 910 at the top of the assembly. Teeth 920 protrude from the bottom of the rotating index ring driver 910 and interact with lower teeth 925 on a rotating index ring 930. The lower teeth 925 move over protrusions 933 in the internal portion of the base 915 and fit into slots 935 when the assembly is in the locked configuration. The teeth 920 that protrude from the rotating index ring 910 are angled on both sides, such that they resemble a component of a picket fence configuration. The lower teeth 925 on the rotating index ring 930 are angled towards only one direction, such that there is directionality in the rotation of the rotating index ring 930. The protrusions 933 that line the slots 935 resemble larger versions of the teeth 920.

FIG. 10 shows a second alternate locking mechanism design for a valve assembly. The design of FIG. 10 is distinct from the design in FIG. 9 in that the teeth 1020 in the index ring driver 1010 are shaped as elongated hexagons and the lower teeth 1025 on the index ring 1030 have receiving recesses 1027. The bottom portions of the teeth 1025 are angled to move over ribs 1035 that are located in the base 205 and protrude into the inner portion of the base.

Figure 11A:
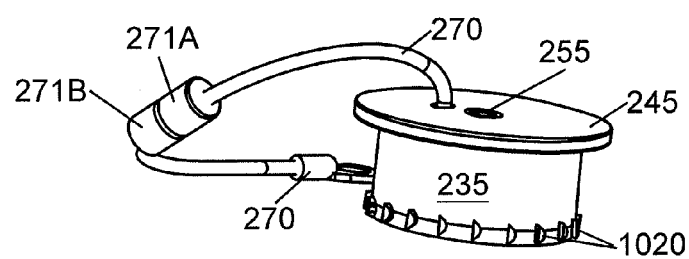
FIG. 11A is an exploded view of an exemplary valve assembly.
Figure 11B:
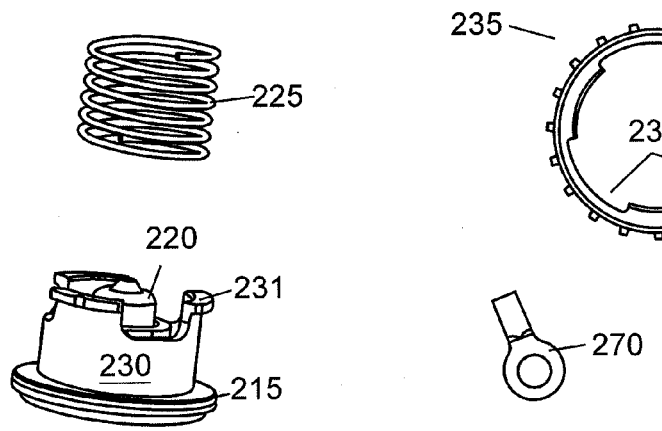
FIG. 11B is a cross sectional view of a portion of the valve assembly in FIG. 11A.

FIGS. 11A and 11B show an embodiment of a valve assembly insert 210 in which the inner containment ring 230 has a plurality of tabs 231 and in which the latching actuating ring 235 has receiving cut outs 232 sized to receive the tabs 231. The receiving cut outs 232 are a part of a securing lip on the latching actuating ring 235. The tabs 231 can be uniformly sized and spaced at the top of the inner containment ring 232, or the tabs 231 can be arranged in a particular pattern that fits a corresponding pattern in the receiving cut outs 232 in the latching actuating ring 235. The interaction between the tabs 231 and receiving cut outs 232 can allow the spring loaded insert assembly 210 to be assembled and disassembled quickly and for parts such as the one-way valve 220 and spring 225 to be easily exchanged with replacement parts, if needed.

Also shown in FIG. 11A is a quick release connection in the lanyard 270 with a first portion 271A and a second portion 271B. The first portion 271A connects to the top cap 245, and the second portion 271B connects to the prosthesis. The quick release connection can include one or more magnets, such as rare earth magnets, snap fittings, pressure fittings, and the like. The lanyard 270 may be a suitably length to allow the latching actuating ring 235 and the top cap 245 to fit into the inner containment ring 230. In some implementations of a valve assembly, the lanyard 270 can be suitably short, such as about 7 cm or less, about 6 cm or less, or the like, and in such implementation, can also include a quick release connection. The lanyard 270 can be of any suitably durable, flexible material, such as stranded metal wire, aramid fiber, polymer fiber, ceramic fiber, woven material, or any combination thereof.

Figure 12:
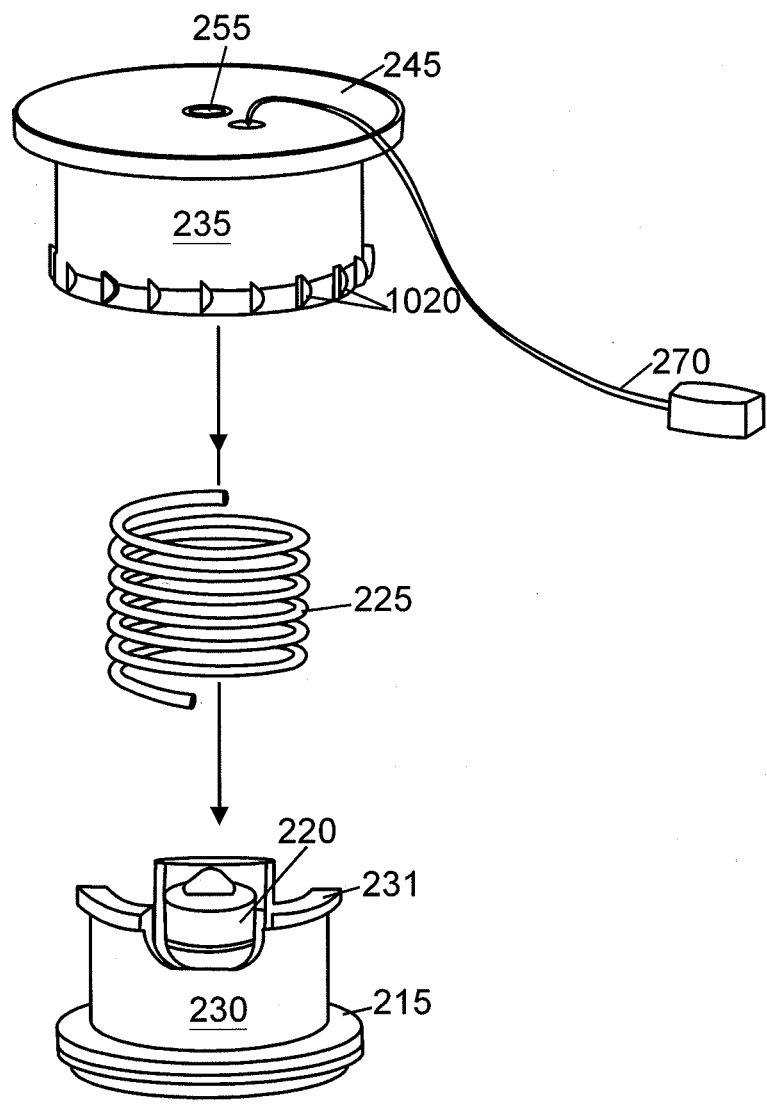
FIGS. 12 and 13 show exploded views of an exemplary valve assembly.
Figure 13:
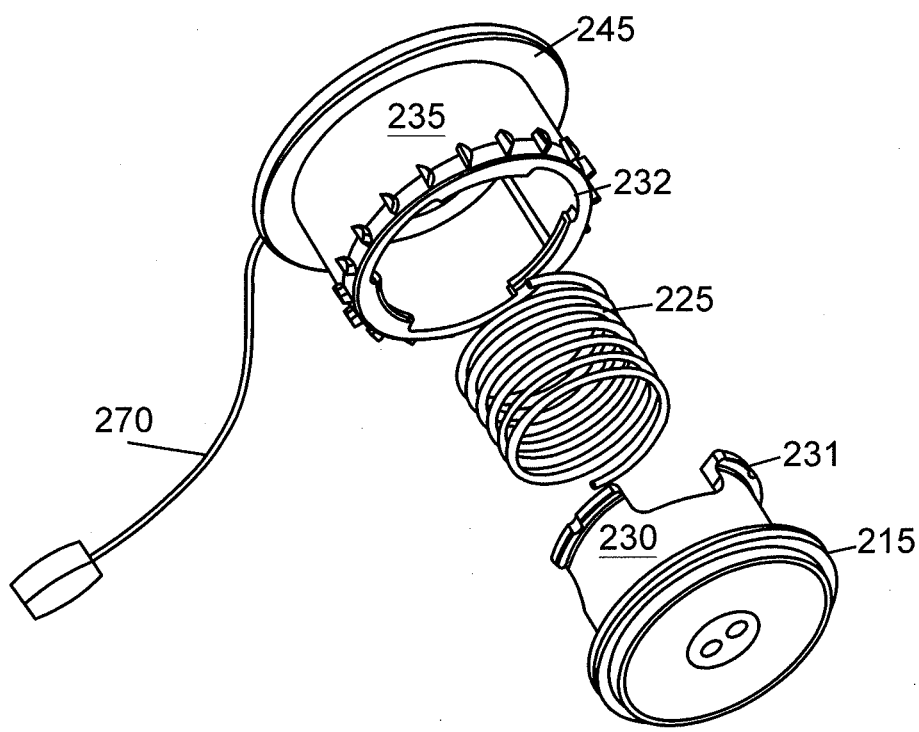

FIGS. 12 and 13 show exploded views of an implementation of a valve assembly similar to that shown in FIGS. 11A and 11B. The valve assembly shown has a latching actuating ring 235 with a top cap 245 that has an air passage 255 and to which a lanyard 270 is attached. The bottom portion of the latching actuating ring has teeth 1020 and a lip that has receiving cut outs 232. The latching actuating ring 235 mates with an inner containment ring 230, outside a spring 225 and a one-way valve 220. The inner containment ring 230 can surround the spring 225. On the bottom portion of the inner containment ring 230 there is a bottom cap 215; the top of the inner containment ring 230 has tabs 231 that are configured to match the receiving slots 232. To assemble the valve assembly, the valve 220 and spring 225 are aligned within the latching actuating ring 235 and inner containment ring 230. The tabs 231 are positioned to fit into the receiving slots 232 so that the latching actuating ring 235 can compress the spring 225 and be lowered over the inner containment ring 230. A user can then rotate either the inner containment ring 230, the latching actuating ring 235, or both until the tabs 231 no longer align with the receiving slots 232 in at least a partial fashion, such that the inner containment ring 230 and latching actuating ring 235 cannot be disengaged without further rotation. When the tabs 231 are not aligned with the receiving slots 232, repeated translation of the latching actuating ring 235 over the inner containment ring 230 will not cause disengagement of the two boss portions 230, 235.

Figure 14A:
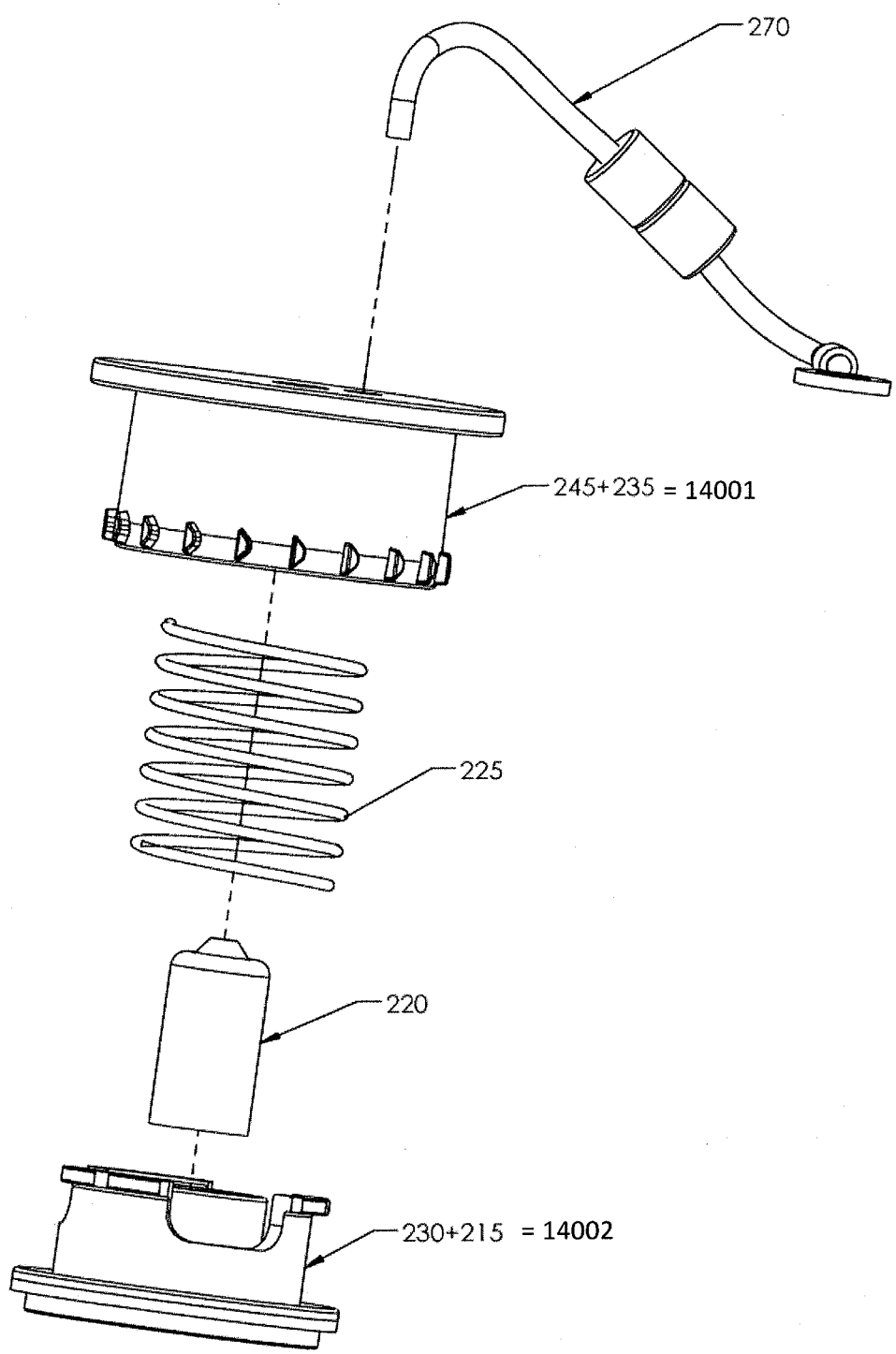

FIGS. 14A-D show another implementation of a valve assembly. In FIG. 14A, an exploded view of an implementation of a valve assembly is shown. The valve assembly has a latching actuating ring 235 with an integral top cap 245. A lanyard is attached to the top of the latching actuating ring and top cap 14001. The spring 225 and one way valve 220 that are present in other implementation of valve assemblies described herein are also present in FIG. 14A. An inner containment ring 230 with an integrated bottom cap 215 is also shown (in this FIG. 14002).

FIG. 14B shows the valve assembly of FIG. 14A in a compressed state. FIG. 14D is a cross-sectional view of the valve assembly of FIG. 14B, with the valve sectioned along the line A. FIG. 14C shows the base 205 partially exploded so that a rotating latch ring 240 and a retaining ring 205A can be seen integrated into one part, a snap fit rotating latch ring 14003. As shown in FIG. 14C, notches 14004 are present in the snap fit rotating latch ring 14003 that can allow it to snap fit into the base 205 and to be held within the base 205 while the valve assembly is in use. However, in some implementations, a rotating latch ring 240 and a retaining ring 205A can be integrated into one part that does not include notches, but that one, integrated part can still be capable of snap fitting into the base 205.

The valve assembly is an insertion valve that can be suitable for amputees of all levels. The valve assembly operates as follows. A loaded spring portion, or insert, is depressed into a base portion until the spring portion cannot be moved any further. The valve then locks into position. Air that is trapped in the suspension holding a patient's prosthesis in place can be expelled by pushing down on the limb, causing the air to pass through a one-way valve inside the loaded spring portion, or insert. At the point when the patient wishes to remove the prosthetic limb, the valve assembly can be disengaged by depressing the loaded spring portion once again until it cannot be moved any further. The valve then unlatches and the spring pushes the loaded spring portion out of the valve base. A lanyard can keep the loaded spring portion attached to the area around which the valve is located in the prosthesis attachment site.

The locking mechanism used in the valve assembly can include a rotating indexing ring, located in the valve base, and a fixed indexing ring mounted to the spring loaded valve portion. The teeth of the rotating and fixed index rings can be designed to interface with each other. When the spring loaded valve portion, or insert is pushed into the valve base, the fixed ring can align with the rotating ring, and can cause the rotating ring to index and position itself into a locked position as the spring loaded valve portion, or insert, moves upwards and locks the assembly in place. Once locked, the spring-loaded portion, or insert, can create an airtight seal with the base by pushing against a lip on the valve base. A seal (such as a rubber seal) on the bottom of the spring loaded valve portion, or insert, can ensure the airtight seal. A seal can alternatively, or additionally, be located on the lip of the valve base. To remove the spring loaded valve portion, or insert, a patient or user can depress the spring loaded valve portion or insert, once again. The rotating ring can then index into an unlocked position that allows the spring loaded valve portion or insert to be released from the assembly. The spring loaded valve portion or insert can then be freely removed from the valve base.

In some embodiments, the locking mechanism can include two rotating indexing rings mounted to the spring loaded valve portion, or insert, and fixed ribs or teeth on the interior of the base. When the spring loaded valve portion, or insert, is pushed into the valve base, the top rotating indexing ring can cause the lower indexing ring to index, or rotate and move the teeth on the lower indexing ring. Upon indexing, the teeth of the lower rotating indexing ring moves into a position relative to the fixed ribs or teeth on the interior of the base that locks the relative position of the lower indexing ring and the base.

The valve assemblies described herein can be made of metal, plastic, fiberglass, ceramic, fiber reinforced polymer composite material, or any other suitable material of sufficient strength. Such materials can be formed into the various parts of the valve assemblies described herein by injection molding, casting, machining, additive manufacturing, 3D printing, extrusion, welding, or any combination thereof.

Methods for using the valve assemblies described herein can include methods for creating and maintaining negative pressure in an attachment site in a prosthetic limb. Such methods include providing a prosthetic limb that includes a valve assembly, as described in greater detail elsewhere herein. The valve assembly used in methods for creating and maintaining negative pressure in an attachment site can include a base that is outside of a bottom portion that includes an inner containment ring, a one-way valve that fits inside the inner containment ring, a spring that is outside of the one-way valve and fits inside the inner containment ring, a latching actuating ring that includes a top cap and teeth, and an indexing ring driver that interacts with the teeth on the latching actuating ring. The one-way valve can have an inlet and an outlet, and when the valve assembly is in use within the prosthetic, the inlet can be in fluid communication with the volume between the prosthetic attachment site and the patient. The method of creating and maintaining negative pressure in an attachment site can also include actuating (e.g. activating) the valve assembly by pressing down on the top cap of the valve assembly. Pressing down on the top cap causes the latching actuating ring and the base of the valve assembly to move closer together and can cause the teeth on the latching actuating ring and features on the indexing ring to interact. The nature of the teeth and the features on the indexing ring, as well as the nature of the interaction and resulting motion can vary, as described hereinabove.

Though the valve assemblies described herein are discussed primarily in terms of use for prosthesis attachment, such valve assemblies can find use in other applications. Such applications for valve assemblies include use as an industrial pneumatic or hydraulic release valve; as a cartridge valve; as a residential or commercial plumbing valve; as a gas valve; as a lid to a container, storage vessel, chamber, housing, or enclosure; as a mechanical fastener; as pneumatic or hydraulic quick disconnect hose fitting or coupling; as a pipe or tube fitting; as a bottle stopper and the like.

The spring loaded valve portion, or insert, of the valve assemblies described herein can be operated or actuated using an extremity, such as a hand or foot, or a phalange, such as a finger or toe. The spring loaded valve portion, or insert, can also be operated or actuated with a mechanical tool.

The one-way valve used in the valve assemblies described herein can be an elastomeric valve, duckbill valve, umbrella valve, cartridge valve, dome valve, Belleville valve, x-frame valve, ball valve, ball check valve, cross-slit valve, diaphragm valve, swing valve, tilting disk valve, in-line check valve, reed valve, lift-check valve, or a combination valve. The one-way valve can be made of metal, plastic, rubber, silicone, wood, adhesive, fiberglass, fiber composite, or any suitable combination thereof. Though the valve assemblies and associated methods are described herein primarily in terms of including a one-way valve, any other suitable type of valve that allows for air or any other gas to pass from one side to the other side of the valve assembly can be used.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the claims.

What is claimed is:

1. A valve assembly comprising:
   a base;
   a bottom cap configured to fit inside the base;
   an inner containment ring;
   a one-way valve with an inlet and an outlet configured to fit inside the inner containment ring;
   a spring which is outside the one-way valve and fits inside the inner containment ring;
   a latching actuating ring configured to fit over the inner containment ring, the latching actuating ring comprising:
      a top cap configured to be actuated; and
      teeth positioned around an outer, lower portion of the latching actuating ring; and
   a rotating latch ring that is configured to interact with the teeth on the latching actuating ring.

2. The valve assembly of claim 1, wherein the base comprises a threaded outer portion.

3. The valve assembly of claim 1, wherein the bottom cap interfaces with the inlet of the one-way valve.

4. The valve assembly of claim 1, wherein the valve assembly is configured to insert into a recess in an object, the valve assembly further comprising a lanyard connected to the top cap and configured to attach to a point on a surface of the object into which the valve assembly inserts.

5. The valve assembly of claim 4, wherein the object into which the valve assembly inserts is a prosthetic limb.

6. The valve assembly of claim 1, wherein the rotating latch ring comprises a snap fit portion located at a top portion of the rotating latch ring, the snap fit portion configured to maintain the rotating latch ring inside the base when the valve assembly is in use.

7. The valve assembly of claim 1, further comprising a seal on a bottom side of the bottom cap.

8. The valve assembly of claim 1, wherein the inner containment ring comprises tabs and the latching actuating ring comprises receiving cut outs configured to match the tabs.

9. A prosthesis comprising:
   a valve assembly comprising:
      a base;
      a bottom cap configured to fit inside the base;
      an inner containment ring;
      a one-way valve with an inlet and an outlet configured to fit inside the inner containment ring;
      a spring which is outside the one-way valve and fits inside the inner containment ring;
      a latching actuating ring configured to fit over the inner containment ring, the latching actuating ring comprising:
         a top cap configured to be actuated; and
         teeth positioned around an outer, lower portion of the latching actuating ring; and
      a rotating latch ring that is configured to interact with the teeth on the latching actuating ring; and
   a prosthesis attachment site, the valve assembly configured to expel air from a space between the prosthesis and a patient's limb within the prosthesis attachment site.

10. The prosthesis of claim 9, wherein the rotating latch ring comprises a snap fit portion located at a top portion of the rotating latch ring, the snap fit portion configured to maintain the rotating latch ring inside the base when the valve assembly is in use.

11. The prosthesis of claim 9, further comprising a seal on a bottom side of the bottom cap.

12. The prosthesis of claim 9, wherein the inner containment ring of the valve assembly comprises tabs and the latching actuating ring comprises receiving cut outs configured to match the tabs.

13. The prosthesis of claim 9, wherein the rotating latch ring interacts with the teeth of the latching actuating ring through indexing teeth located on the rotating latch ring, the indexing teeth configured to induce a motion of the rotating latch ring when the latching actuating ring is moved vertically over the rotating latch ring.

14. The prosthesis of claim 9, wherein the rotating latch ring comprises upper and lower teeth, the upper teeth shaped as elongated hexagons and the lower teeth having receiving recesses.

15. A suction socket prosthetic valve assembly comprising:
   a top;
   a bottom;
   a base that is part of the bottom of the valve assembly;
   a bottom cap configured to fit inside the base;
   an inner containment ring;
   a one-way valve with an inlet and an outlet configured to fit inside the inner containment ring;
   a spring which is outside the one-way valve and fits inside the inner containment ring;
   a latching actuating ring configured to fit over the inner containment ring, the latching actuating ring comprising:

a top cap that is part of the top of the valve assembly, the top cap configured to be actuated; and teeth positioned around an outer, lower portion of the latching actuating ring; and a rotating latch ring that is configured to interact with the teeth on the latching actuating ring;

wherein the valve assembly is configured to alternatively move into a first position and move into a second position when force is applied to the top to direct it towards the bottom, such that a first applied force causes the valve assembly to move into the first position, and a second applied force causes the valve assembly to move into the second position, wherein the top and bottom are a smaller distance apart in the first position than in the second position.

16. The suction socket prosthetic valve assembly of claim 15, wherein the latching actuating ring and the rotating latch ring interact to alternately move the suction socket prosthetic valve assembly between the first and second positions when force is applied.

17. The suction socket prosthetic valve assembly of claim 15, wherein the rotating latch ring interacts with the teeth of the latching actuating ring through indexing teeth located on the rotating latch ring, the indexing teeth configured to induce a motion of the rotating latch ring when the latching actuating ring is moved vertically over the indexing ring.

18. The suction socket prosthetic valve assembly of claim 15, wherein the rotating latch ring comprises a snap fit portion located at a top portion of the rotating latch ring, the snap fit portion configured to maintain the rotating latch ring inside the base when the valve assembly is in use.

19. A method of creating and maintaining negative pressure in an attachment site in a prosthetic limb, comprising:

providing a prosthetic limb comprising a valve assembly comprising:

a base;

a bottom cap configured to fit inside the base;

an inner containment ring;

a one-way valve with an inlet and an outlet configured to fit inside the inner containment ring;

a spring which is outside the one-way valve and fits inside the inner containment ring;

a latching actuating ring configured to fit over the inner containment ring, the latching actuating ring comprising:

a top cap configured to be actuated; and teeth positioned around an outer, lower portion of the latching actuating ring; and a rotating latch ring that is configured to interact with the teeth on the latching actuating ring.

* * * * *